US012193858B2

(12) United States Patent
Qiang et al.

(10) Patent No.: US 12,193,858 B2
(45) Date of Patent: Jan. 14, 2025

(54) METHOD TO DETECT ENERGY-DEPENDENT COUNT LOSS

(71) Applicant: CANON MEDICAL SYSTEMS CORPORATION, Tochigi (JP)

(72) Inventors: Yi Qiang, Vernon Hills, IL (US); Xiaoli Li, Vernon Hills, IL (US); Wenyuan Qi, Vernon Hills, IL (US)

(73) Assignee: CANON MEDICAL SYSTEMS CORPORATION, Tochigi (JP)

( * ) Notice: Subject to any disclaimer, the term of this patent is extended or adjusted under 35 U.S.C. 154(b) by 183 days.

(21) Appl. No.: 17/870,346

(22) Filed: Jul. 21, 2022

(65) Prior Publication Data

US 2024/0023911 A1 Jan. 25, 2024

(51) Int. Cl.
*A61B 6/42* (2024.01)
*A61B 6/58* (2024.01)
*G01T 1/17* (2006.01)

(52) U.S. Cl.
CPC ............ *A61B 6/4241* (2013.01); *A61B 6/583* (2013.01); *G01T 1/171* (2013.01)

(58) Field of Classification Search
CPC ........ A61B 6/4241; A61B 6/583; G01T 1/171
See application file for complete search history.

(56) References Cited

U.S. PATENT DOCUMENTS

| 2014/0233693 | A1 | 8/2014 | Wang et al. | |
|---|---|---|---|---|
| 2014/0233694 | A1 | 8/2014 | Wang et al. | |
| 2016/0356894 | A1* | 12/2016 | Bhattacharya | A61B 6/037 |
| 2017/0371046 | A1* | 12/2017 | Laurence | G01T 1/249 |
| 2018/0203141 | A1 | 7/2018 | Chang et al. | |
| 2020/0363542 | A1* | 11/2020 | Song | G01T 1/171 |
| 2021/0030387 | A1* | 2/2021 | Andreyev | A61B 6/5282 |
| 2021/0109236 | A1* | 4/2021 | Myers | G01T 1/171 |

FOREIGN PATENT DOCUMENTS

JP 2011-185716 A 9/2011

* cited by examiner

*Primary Examiner* — David P Porta
*Assistant Examiner* — Fani Polyzos Boosalis
(74) *Attorney, Agent, or Firm* — Oblon, McClelland, Maier & Neustadt, L.L.P.

(57) ABSTRACT

A method is provided for count loss correction based on detector dead time in a radiation diagnosis apparatus. The method includes acquiring scan data from a scan of a patient performed using the radiation diagnosis apparatus; determining, from the acquired scan data, a first count rate occurring in a first energy window spanning a first energy range; determining, from the acquired scan data, a second count rate occurring in a second window spanning a second energy range, the second energy range being different from the first energy range; calculating a particular count loss correction factor based on the determined first count rate and the determined second count rate; and reconstructing an image based on the acquired scan data and the calculated particular count loss correction factor.

17 Claims, 7 Drawing Sheets

METHOD TO DETECT ENERGY-DEPENDENT COUNT LOSS

BACKGROUND

Field

The present disclosure relates a method for count loss correction due to detector dead time in a radiation diagnosis apparatus such as a Positron Emission Tomography (PET) diagnostic apparatus.

Description of the Related Art

A photon detector usually need time to respond to an incoming photon, process a corresponding signal, and digitize the corresponding value of the processed signal. During a certain amount of time following a first event, the detector will not be able to register other events, which defines the detector's dead time. Thus, it is important to accurately estimate and correct for such dead time when using a photon detector to measure a concentration of a high activity source. The dead time is usually estimated based on the measured event rate using a particular dead-time model, e.g. a paralyzable model, a non-paralyzable model, a hybrid model, etc.

For example, using a paralyzable dead time model, the measured singles count rate can be expressed as $$f_{measured} = f_{detected} \cdot e^{-f_{detected} \cdot t_{deadtime}}, \quad (1)$$

where $f_{detected}$ is the rate (in counts per second (cps)) at which the photons are being detected by the detector and $t_{deadtime}$ is the detector dead time for each detected count. During reconstruction, a correction factor is applied to the measured count rate to estimate the actual detected count rate using:

$$f_{detected} = f_{measured} \cdot C_{single}(f_{measuerd}), \quad (2)$$

where $C_{single}(f_{measured})$ is the singles Count Loss Correction (CLC) factor and is usually greater than one. Based on equation (1), the explicit analytical form of $C_{single}(f_{measured})$ does not exist. Therefore, in practice, either an approximated analytical form or a lookup table is used instead.

In PET reconstruction, since pairs of photon events are used, the pairs Count Loss Correction (CLC) factor needs to be calculated. For most systems, the pairs CLC factor for an event with singles a and b is given by $$C_{pair}(a,b) = C_{single}(f_a) \cdot C_{single}(f_b), \quad (3)$$

where $f_a$ and $f_b$ are the count rates of each detector. The pairs CLC factor can be either estimated and applied on an event-by-event basis in the reconstruction process, or an average pairs CLC factor can be calculated and applied as a scaling factor to the reconstructed image.

The overall pairs CLC factor can be further simplified as a function of the system singles rate as:

$$C_{pair} = C_{pair}(f_{total\ singles}) = C_{single}^2(f_{total\ singles}). \quad (4)$$

For a system where the count loss from different detectors is correlated, the estimation of the pairs CLC factor is more complicated.

If using a constant dead time for count loss correction and ignoring phantom/patient dependency, an error in quantitative measurement will occur at high count rates, when the phantom/patient is very different from what is used for the initial dead time calibration.

SUMMARY

An embodiment of the present disclosure is directed to a method for count loss correction based on detector dead time in a radiation diagnosis apparatus. The method includes acquiring scan data from a scan of a patient performed using the radiation diagnosis apparatus; determining, from the acquired scan data, a first count rate occurring in a first energy window spanning a first energy range; determining, from the acquired scan data, a second count rate occurring in a second window spanning a second energy range, the second energy range being different from the first energy range; calculating a particular count loss correction factor based on the determined first count rate and the determined second count rate; and reconstructing an image based on the acquired scan data and the calculated particular count loss correction factor.

Another embodiment of present disclosure is directed to a radiation diagnosis apparatus, comprising: circuitry configured to acquire scan data from a scan of a patient performed using a scanning apparatus of the radiation diagnosis apparatus, determine, from the acquired scan data, a first count rate occurring in a first energy window spanning a first energy range; determine, from the acquired scan data, a second count rate occurring in a second window spanning a second energy range, the second energy range being different from the first energy range; calculate a particular count loss correction factor based on the determined first count rate and the determined second count rate; and reconstruct an image based on the acquired scan data and the calculated particular count loss correction factor.

A further embodiment of present disclosure is directed to A method for count loss correction based on detector dead time in a radiation diagnosis apparatus, the method comprising: acquiring, for each detector of a plurality of detectors in the radiation diagnosis apparatus, corresponding detector scan data for the detector, from a scan of a patient performed using the radiation diagnosis apparatus; determining, for each detector of the plurality of detectors from the corresponding detector scan data, a first detector count rate occurring in a first energy window spanning a first energy range; determining, for each detector of the plurality of detectors from the corresponding detector scan data, a second detector count rate occurring in a second window spanning a second energy range, the second energy range being different from the first energy range; calculating, for each detector of the plurality of detectors, a detector count loss correction factor, based on the determined detector first count rate for the detector and the determined second detector count rate for the detector; calculating a particular count loss correction factor based on the calculated plurality of detector count loss correction factors corresponding to the plurality of detectors; and reconstructing an image based on the acquired scan data and the calculated particular count loss correction factor.

BRIEF DESCRIPTION OF THE DRAWINGS

The application will be better understood in light of the description which is given in a non-limiting manner, accompanied by the attached drawings in which.

DETAILED DESCRIPTION

Figure 1A:
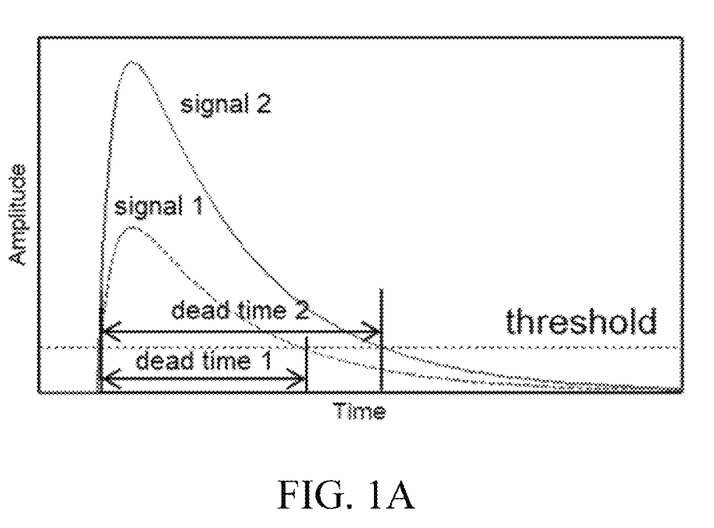
FIGS. 1A and 1B illustrate the energy dependence of dead time for a photon detector.
Figure 1B:
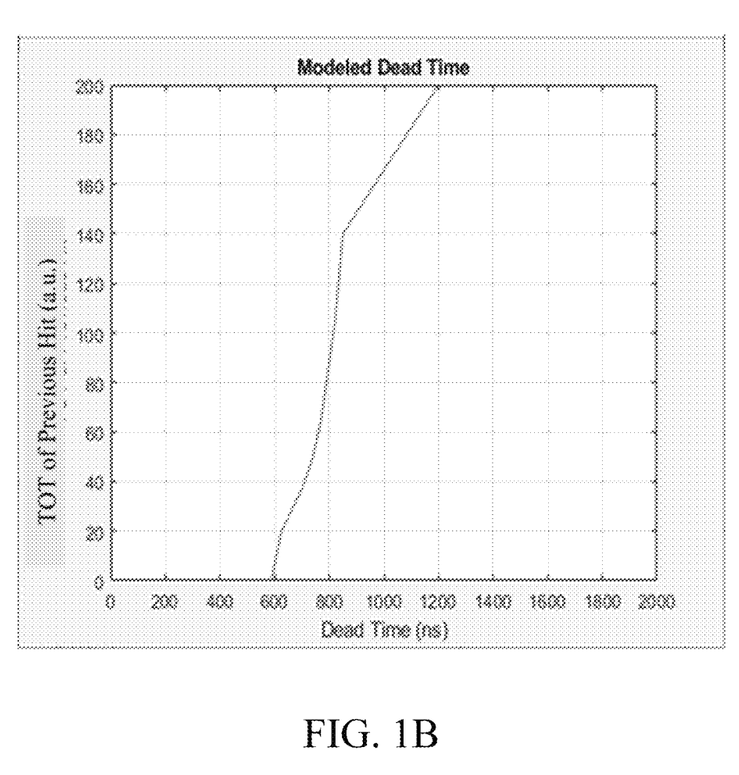

As shown in FIGS. 1A and 1B, the dead time for a photon detector normally depends on the energy of an event measured by the photon detector. Using a comparator used in the timing measurement as an example, when the signal is above the threshold of the comparator, any other signal within the time-over-threshold (TOT) will not trigger a new timing measurement. Therefore, the dead time for the detector correlates with a time period a signal is over the threshold, which in turn depends on the amplitude of the signal, and hence the energy of the first event, as shown in FIG. 1A.

In PET scans, the detected energy spectrum of the photons, as detected by a detector, depends on the object being scanned, due to scattering and absorption. Therefore, if the detector has an energy-dependent dead time, the count loss correction is phantom/patient dependent. Otherwise, a systematic error would occur, as discussed below.

Figure 2:
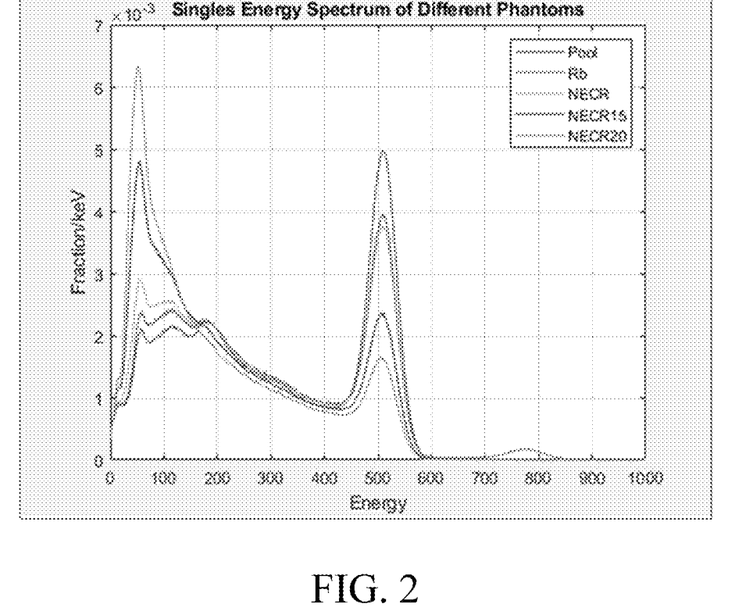
FIG. 2 is a diagram illustrating the measured energy spectrum for different phantoms.

For example, for the five different example phantoms shown in Table 1, the observed singles energy spectrum is shown in FIG. 2.

TABLE 1

| Phantom Name | Description |
| --- | --- |
| Pool | A cylindrical phantom filled with water with certain F-18 concentration. The water volume is 30 cm long and 10 cm in radius. The plastic wall is 1.5 mm thick. |
| Rb | A voxelized patient phantom injected with Rb. |
| NECR | A cylindrical NECR scattering phantom, 70 cm long and 10 cm in radius, with an inserted FDG line source off-center by 45 mm. |
| NECR15 | Extend the radius of NECR scattering phantom to 15 cm. |
| NECR20 | Extend the radius of NECR scattering phantom to 20 cm. |

Figure 3A:
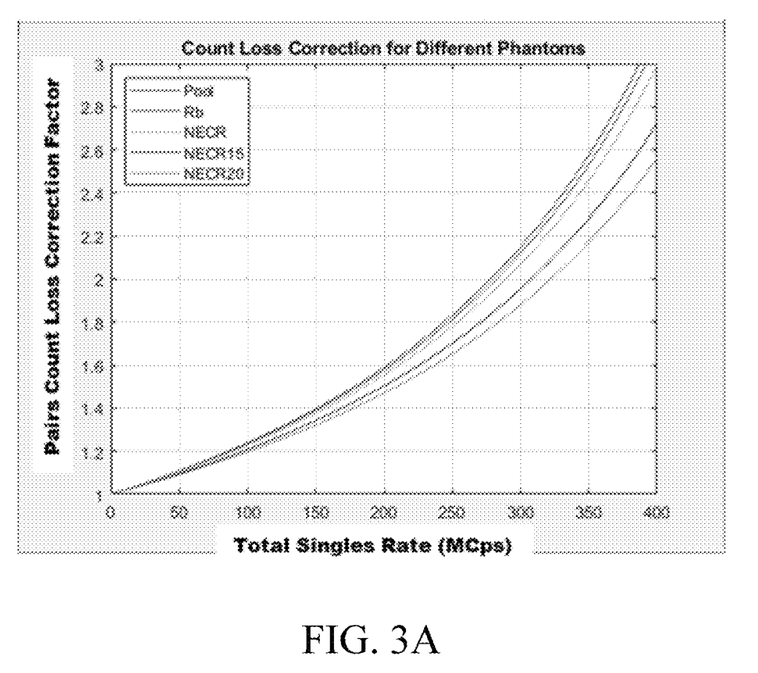
FIG. 3A illustrates that different pairs count loss correction factors, as a function of the total singles rate, are needed for various phantoms, due to patient/phantom dependence on dead time.
Figure 3B:
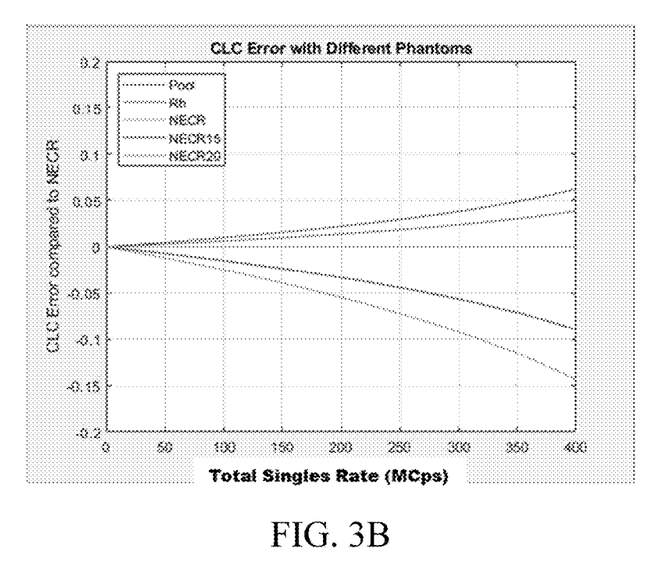
FIG. 3B is a diagram illustrating the CLC error for different phantoms, compared to a reference phantom, as a function of the total singles rate, using a method that ignores patient/phantom dependence on dead time.

Thus, if a conventional count loss correction model is used and phantom/patient dependency is ignored, an error in the quantitative measurement will occur at high count rates when the phantom/patient is very different from what is used to calibrate the count loss correction. For example, FIG. 3A illustrates the pairs count loss correction (CLC) factor as a function of the total singles rate for the five phantoms of Table 1 (assuming use of a common CLC curve calibrated with the NECR phantom), while FIG. 3B illustrates the resulting CLC error (with respect to the NECR phantom) for each of the other phantoms, as a function of the total singles rate. As illustrated in FIG. 3B, the error in quantification of the other phantom images will grow to more than 10%.

Thus, in one embodiment, a plurality of counters are used to measure singles event rates within different energy windows, and the measured count rates are used to determine a more accurate CLC factor to correct for count loss, so as to achieve better quantitative accuracy across a broad range of patients.

Ideally, the average dead time a detector experiences can be expressed as $$\tau_{average} \cdot f_{total} = \int \tau(E) f(E) dE, \quad (5)$$

where $\tau(E)$ is the dead time caused by a previous single event with energy E, and f(E) is the energy distribution of detected photons. If the energy spectrum can be measured and the dead time as a function of energy is known, the average dead time can be calculated numerically.

In reality, the full energy spectrum is usually not measured. However, in one embodiment, Equation 5 can be approximated by a weighted sum with counts measured with fewer energy windows:

$$\tau_{average} \cdot f_{total} \approx \Sigma \tau_i w_i f_i \approx \tau_o \Sigma w_i f_i = \tau_o f_{effective}, \quad (6)$$

where $\tau_0$ is a constant dead time, $f_i$ is the count rate within each energy window i, and $w_i$ is the weight applied to each count rate i. Here, we define a new quantity, called the effective singles rate (ESR):

$$f_{effective} = \Sigma w_i f_i. \quad (7)$$

By constructing the effective singles rate, which absorbs all the phantom/patient dependency in the dead time calculation, we can now rely on a common CLC curve $C(f_{effective})$ to address a wide range of scan conditions.

Figure 4:
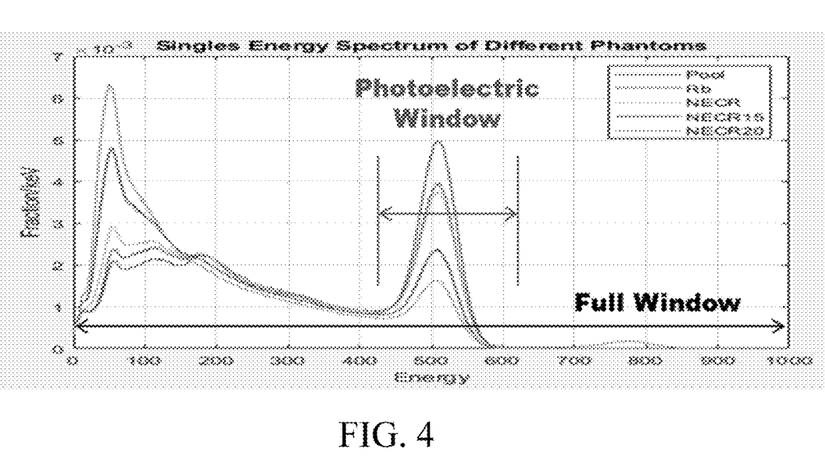
FIG. 4 is a diagram illustrating a photoelectric window and a full window within energy spectrums for various phantoms.

In one embodiment, event rates within different windows are measured. For example, as shown in FIG. 4, the photoelectric (PE) window and the full-energy window are used to measure the PE rate $f_{PE}$ and the total event rate $f_{total}$. In one embodiment, both rates are aggregated total system rates from all detectors and are measured for each PET scan. Consistent with the present disclosure, other windows can be used to determine other corresponding event rates.

The combined effective event rate $f_{effective}$ is then calculated as a linear combination of the two measured rates:

$$f_{effective} = \alpha \cdot f_{PE} + \beta \cdot f_{total}. \quad (8)$$

Figure 5A:
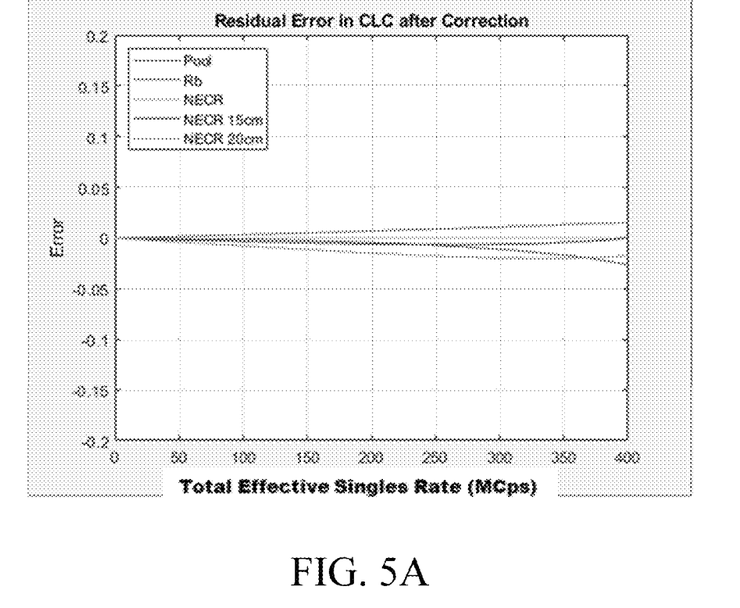
FIG. 5A is a diagram illustrating the CLC error for different phantoms, compared to a reference phantom, as a function of the total singles rate, using a method according to the present disclosure.
Figure 5B:
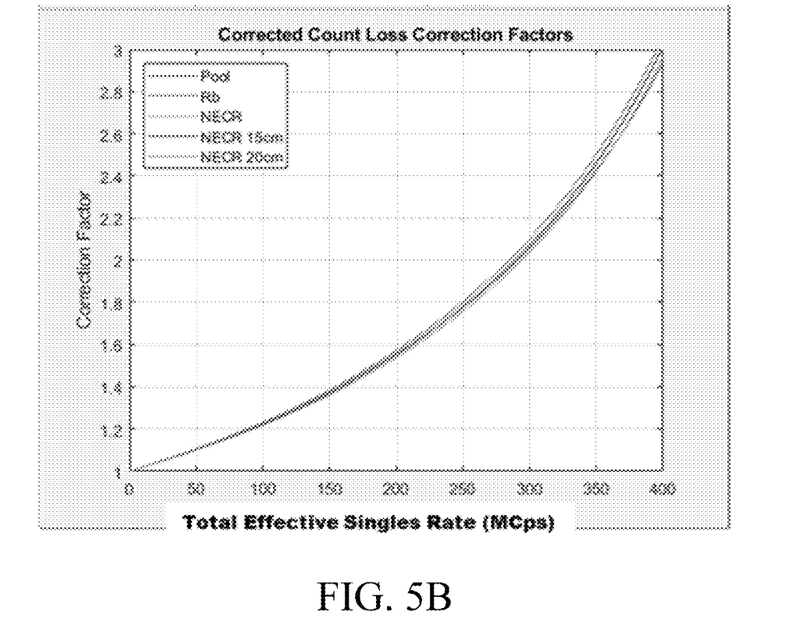
FIG. 5B is an illustration of the pairs count loss correction factor as a function of the total singles rate for various phantoms, using a method according to the present disclosure.

Here, the linear coefficients $\alpha$ and $\beta$ are calibrated for each particular detector system by minimizing the error in count loss correction using different phantoms, for example. FIG. 5A illustrates an example result of this process in which the residual CLC error as a function of the corrected singles rate is jointly minimized for the five different phantoms of Table 1 by optimizing the values of $\alpha$ and $\beta$ to minimize divergence or minimize the average error, for example. FIG. 5B illustrates the resulting corrected CLC curves (as a function of the corrected singles rate) for the five different phantoms.

The final pairs CLC curve can be an average of all CLC curves, or can be derived from a typical phantom in the middle range, e.g. the NECR phantom. The effective singles rate method described in this disclosure ensures the count loss correction is accurate to within +−3%.

For each scan, the effective singles rate is first measured, and then a CLC factor is determined based on the CLC curve. Finally, the average pairs CLC factor is applied to the reconstructed image, e.g., via multiplication.

Figure 6:
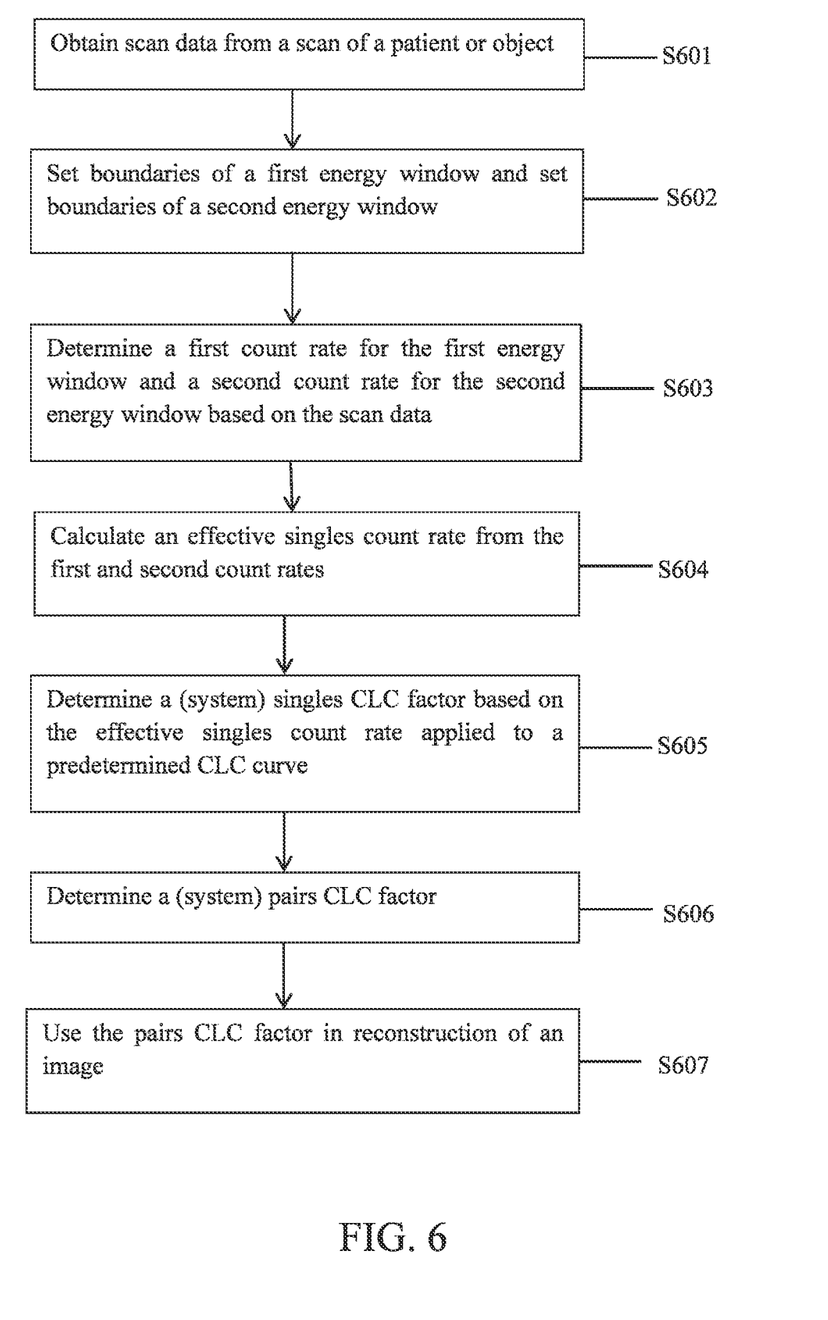
FIG. 6 is a flowchart of a method according to the present disclosure.

In particular, FIG. 6 is a flowchart of a CLC correction process according to one embodiment of the present disclosure.

In step S601, scan data from a scan of a patient or object is obtained. The scan data is obtained for a plurality of detectors in the radiation diagnosis apparatus, e.g., a PET scanner.

In step S602, a first energy window and a second energy window are defined. For example, as shown in FIG. 4, the first window can be a photoelectric (PE) window (photopeak window) surrounding a peak energy, e.g., 511 keV for PET. Further, the second energy window can be the full energy spectrum.

In step S603, a first count rate for the first energy window (e.g., the PE count rate $f_{PE}$) and a second count rate for the second energy window (e.g., the total event rate $f_{total}$) are determined from the obtained scan data. In one embodiment, both rates are aggregated total system rates from all detectors and are measured for each PET scan.

In step S604, the effective singles rate (ESR) is calculated using Equation (8) as a linear combination of $f_{PE}$ and $f_{total}$:

$$f_{effective} = \alpha \cdot f_{PE} + \beta \cdot f_{total}.$$

The coefficients $\alpha$ and $\beta$ are predetermined through an optimization process using multiple phantoms, for example, and are stored in a memory.

In step S605, a predetermined CLC function C is used to find a CLC factor given the calculated effective single rate, i.e., the CLC factor is $C(f_{effective})$. In an alternative embodiment, step S605 can be skipped and a pairs CLC factor can be directly determined from the pairs CLC curve, based on the effective singles count rate.

In step S606, the overall pairs CLC factor is determined according to Equation (4), for example, using:

$$C_{pair} = C_{pair}(f_{total\ singles}) = single^2(f_{total\ singles}).$$

In one embodiment, an average pairs CLC factor can be calculated and applied as a scaling factor to the reconstructed image. Alternatively, a pairs CLC factor can be applied for each LOR in the reconstruction process.

In step S607, the determined pairs CLC factor is used to correct the counts in the reconstruction of an image.

In the one embodiment, as described above, a total effective singles rate is measured and calculated in an imaging system, and is used to determine a global pairs CLC factor for reconstruction of an image. However, the method of calculating the effective singles rate can be applied to singles count loss correction or pairs count loss correction.

Further, in an alternative embodiment, a singles CLC factor can be determined for each individual detector element based on the count rates for the individual detector element. In particular, a measured energy spectrum for each detector is used to determine $f_{effective}$ and thus the singles CLC factor for the detector. The effective singles rate and singles CLC factor are determined for each detector, and the detectors can either share a common CLC curve/LUT, or each detector can have its own CLC curve/LUT. In this embodiment, a system singles CLC or pairs CLC factor is then formulated by combining all the singles CLC factors of the individual detectors.

In another embodiment, the predetermined CLC function C used in step S605 can take the form of a multi-dimensional function or a look-up-table by taking the count rates from different windows as direct input, i.e., using a function $C(f_1, f_2, \ldots)$, where $f_1$, $f_2$ are, for example, $f_{PE}$ and $f_{total}$.

In another embodiment, a singles CLC factor or a pairs CLC factor can be determined for each segment of a scan, e.g., 1 second segment of a 10 second scan, for better accuracy when the count rate changes dramatically during the scan.

In another embodiment, the number and/or the ranges of the energy windows can be further optimized to reduce phantom/patient dependence. In one embodiment, the PE window and the full energy window are chosen for simplicity as they are generally available already. However, in order to allow the scanner to operate with a much wider range of applications, both the number and the range of the windows can be optimized.

In another embodiment, instead of the singles count rate, other measured quantities reflecting count rate, e.g., data rate, detector power supply current, HV current, equivalent weighted average count rates, etc. can be used. In this case, the method includes determining, from the acquired scan data, a first measured quantity related to a first energy range; determining, from the acquired scan data, a second measured quantity related to a second energy range, the second energy range being different from the first energy range, or the second measured quantity relating to the first energy range, but differently from the first measured quantity; and calculating a particular count loss correction factor based on the determined first measured quantity and the determined second measured quantity.

The methods of the present disclosure have several advantages over existing methods, including providing a more accurate determination of CLC factors and improved quantitative measurements of concentrations (distribution of injected dose in patient) in a straightforward implementation. For example, a 10% error in a CLC factor translates to a 10% error in image quantification.

Figure 7:
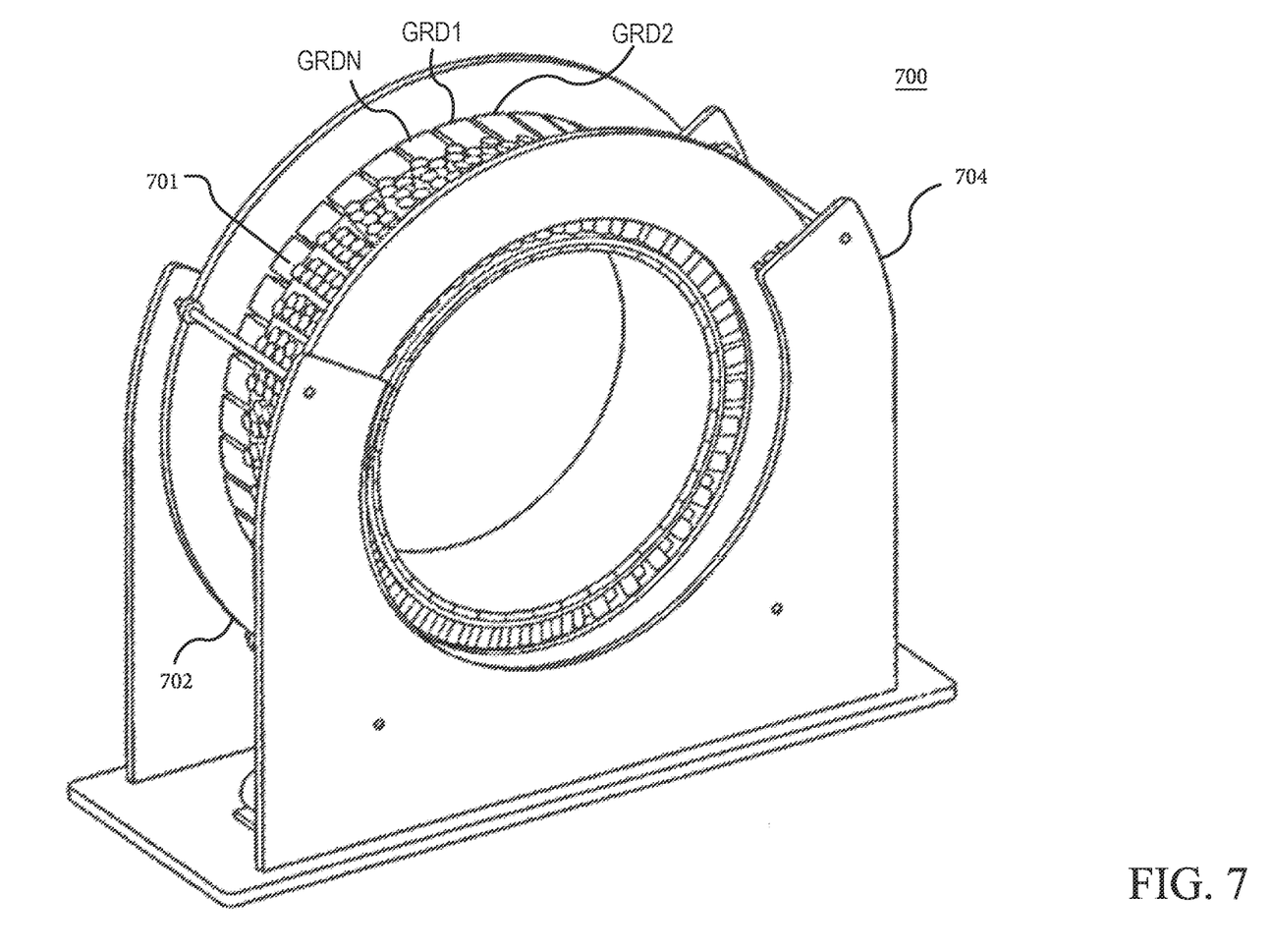
FIG. 7 is an illustration of a perspective view of a positron emission tomography (PET) scanner according to one embodiment of the present disclosure.
Figure 8:
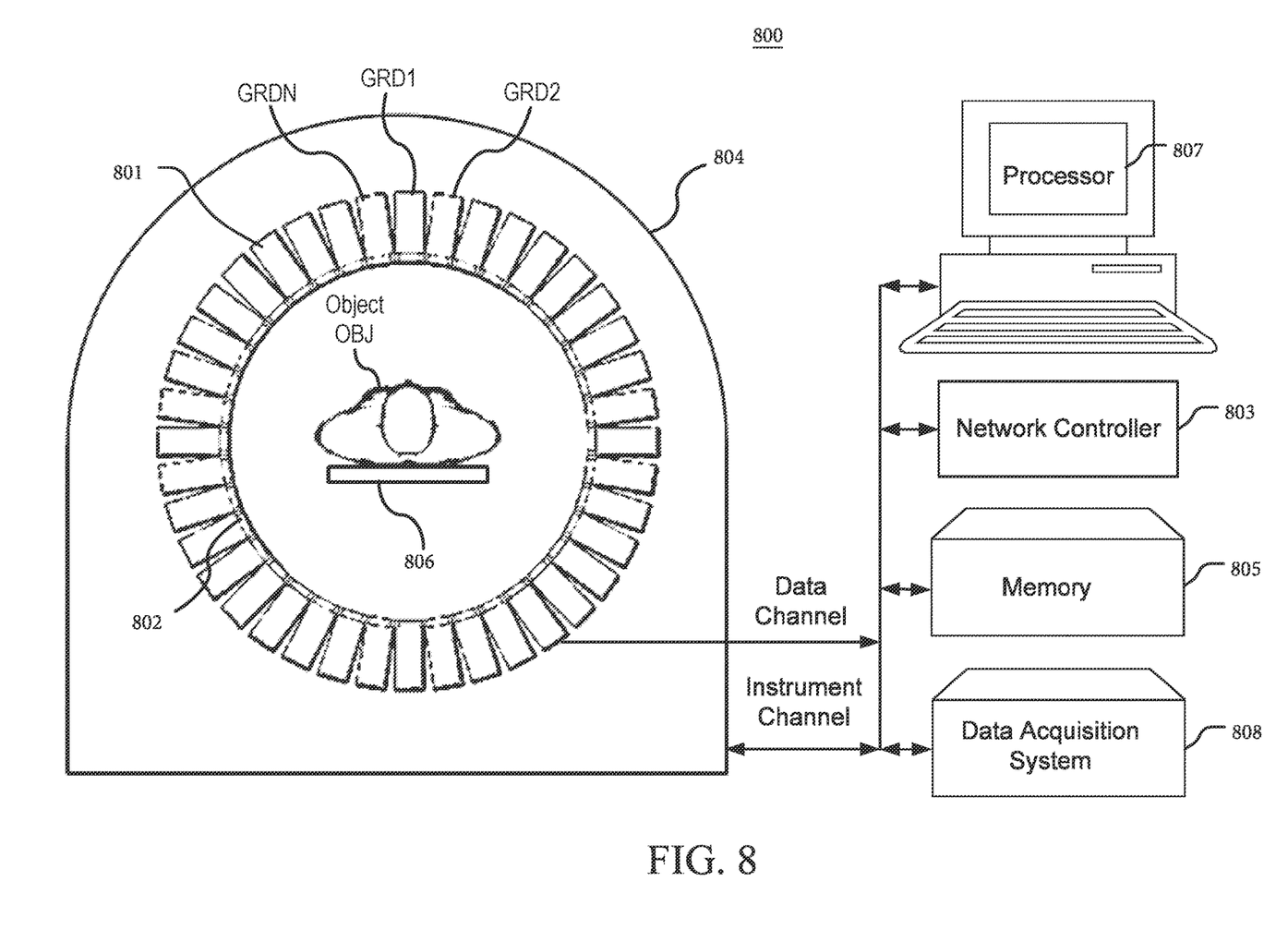
FIG. 8 is a schematic of a PET scanner apparatus and associated hardware, according to one embodiment of the present disclosure.

A PET scanner that can be used in conjunction with the embodiments disclosed herein is shown in FIGS. 7 and 8. PET scanner 700 includes a plurality of gamma-ray detectors (GRDs) 101 (e.g., GRD1, GRD2, through GRDN) that are each configured as rectangular detector modules. According to one implementation, the detectors are arranged in a ring, which forms a circular bore 102 about a gantry 104. In this example, the ring includes 40 GRDs 701. A ring may have a different number of GRDs 701 depending on factors such as the desired size of bore 702. The GRDs 701 include scintillator crystal arrays for converting the gamma rays into scintillation photons (e.g., at optical, infrared, and ultraviolet wavelengths), which are detected by photodetectors. Each GRD 701 can include a two-dimensional array of individual detector crystals, which absorb gamma radiation and emit scintillation photons, or can include a monolithic array or a slatted array. The scintillation photons can be detected by a two-dimensional array of devices such as SiPMs (not shown) that are also arranged in the GRD 701. A light guide can be disposed between the array of detector crystals and the SiPMs.

FIG. 7 shows a schematic view of a PET scanner system having GRDs arranged to detect gamma-rays emitted from an object OBJ. The GRDs can measure the timing, position, and energy corresponding to each detected gamma-ray. It can be appreciated that the single PET detector ring of FIG. 7 can be extrapolated to include any number of PET detector rings along an axial length of the PET scanner.

FIG. 8 shows an example of the arrangement of a PET scanner 800, in which the object OBJ to be imaged rests on a table 806 and the GRD modules GRD1 through GRDN are arranged circumferentially around the object OBJ and the table 806. The GRDs may comprise a PET detector ring and may be fixedly-connected to a circular bore 802 that is fixedly-connected to a gantry 804. The gantry 804 houses many parts of the PET scanner. The gantry 804 of the PET scanner also includes an open aperture, defined by the cylindrical bore 802, through which the object OBJ and the table 806 can pass, and gamma-rays emitted in opposite directions from the object OBJ due to an annihilation event can be detected by the GRDs and timing and energy information can be used to determine coincidences for gamma-ray pairs.

In FIG. 8, circuitry and hardware are also shown for acquiring, storing, processing, and distributing gamma-ray detection data. The circuitry and hardware include a processor 807, a network controller 803, a memory 805, and a data acquisition system (DAS) 808. The PET imager also includes a data channel that routes detection measurement results from the GRDs to the DAS 808, the processor (processing circuitry) 807, the memory 805, and the network controller 803. The data acquisition system 808 can control the acquisition, digitization, and routing of the detection data from the detectors. In one implementation, the DAS 808 controls the movement of the table 806. The processor 807 performs functions including identifying arrangement errors, pre-reconstruction processing of the detection data, image reconstruction, and post-reconstruction processing of the image data.

According to an embodiment, the processor 807 of the PET scanner 800 of FIG. 8 can be configured to perform the methods as described herein. The processor 807 can include a CPU that can be implemented as discrete logic gates, as an Application Specific Integrated Circuit (ASIC), a Field Programmable Gate Array (FPGA) or other Complex Programmable Logic Device (CPLD). An FPGA or CPLD implementation may be coded in VHDL. Verilog, or any other hardware description language and the code may be stored in an electronic memory directly within the FPGA or CPLD, or as a separate electronic memory. Further, the memory 805 can be a hard disk drive, CD-ROM drive, DVD drive. FLASH drive. RAM, ROM or any other electronic storage known in the art. The memory 805 may be non-volatile, such as ROM, EPROM, EEPROM or FLASH memory. The memory 805 can also be volatile, such as static or dynamic RAM, and a processor, such as a microcontroller or microprocessor, may be provided to manage the electronic memory as well as the interaction between the FPGA or CPLD and the memory.

Alternatively, the CPU in the processor 807 can execute a computer program including a set of computer-readable instructions that perform methods described herein, the program being stored in any of the above-described non-transitory electronic memories and/or a hard disk drive, CD, DVD, FLASH drive or any other known storage media. Further, the computer-readable instructions may be provided as a utility application, background daemon, or component of an operating system, or combination thereof, executing in conjunction with a processor, such as a Xenon processor from Intel or an Opteron processor from AMD and an operating system, such as Microsoft VISTA, UNIX, Solaris, LINUX, Apple, MAC-OS and other operating systems known to those skilled in the art. Further, the CPU can be implemented as multiple processors cooperatively working in parallel to perform the instructions. The instructions may be stored in memory 25 or within a memory located in controller 203 (not shown).

In one implementation, the PET scanner may include a display for displaying a reconstructed image and the like. The display can be an LCD display, CRT display, plasma display, OLED, LED or any other display known in the art.

The network controller 803, such as an Intel Ethernet PRO network interface card from Intel, can interface between the various parts of the PET imager. Additionally, the network controller 803 can also interface with an external network. As can be appreciated, the external network can be a public network, such as the Internet, or a private network such as an LAN or WAN network, or any combination thereof and can also include PSTN or ISDN sub-networks. The external network can also be wired, such as an Ethernet network, or can be wireless such as a cellular network including EDGE, 3G and 4G wireless cellular systems. The wireless network can also be WiFi, Bluetooth, or any other wireless form of communication that is known.

Additional embodiments are provided by way of example in the following parentheticals.

(1) A method for count loss correction based on detector dead time in a radiation diagnosis apparatus, the method comprising:
acquiring scan data from a scan of a patient performed using the radiation diagnosis apparatus;
determining, from the acquired scan data, a first count rate occurring in a first energy window spanning a first energy range;
determining, from the acquired scan data, a second count rate occurring in a second window spanning a second energy range, the second energy range being different from the first energy range;
calculating a particular count loss correction factor based on the determined first count rate and the determined second count rate; and
reconstructing an image based on the acquired scan data and the calculated particular count loss correction factor.

(2) The method of (1), wherein the step of determining the first count rate comprises determining, as the first count rate, a total count rate from all detectors in the radiation diagnosis apparatus in the first energy window, which is a photoelectric window.

(3) The method of (1), wherein the step of determining the second count rate comprises determining, as the second count rate, a total count rate from all detectors in the radiation diagnosis apparatus in the second energy window, which spans an entirety of the energy spectrum for the radiation diagnosis apparatus.

(4) The method of (1), wherein the calculating step further comprises calculating an effective singles count rate as a weighted combination of the first count rate and the second count rate.

(5) The method of (4), wherein the step of calculating the effective singles count rate comprises calculating the effective singles count rate using weights that are predetermined so as to minimize a count loss correction error calculated for a plurality of phantoms.

(6) The method of (4), wherein the calculating step further comprises determining a singles count loss correction factor based on the calculated effective singles count rate by applying the calculated effective singles count rate to a predetermined count loss correction function.

(7) The method of (6), wherein the calculating step further comprises determining, as the particular count loss correction factor, a pairs count loss correction factor, based on the determined singles count loss correction factor.

(8) A method for count loss correction based on detector dead time in a radiation diagnosis apparatus, the method comprising:
acquiring, for each detector of a plurality of detectors in the radiation diagnosis apparatus, corresponding detector scan data for the detector, from a scan of a patient performed using the radiation diagnosis apparatus;
determining, for each detector of the plurality of detectors from the corresponding detector scan data, a first detector count rate occurring in a first energy window spanning a first energy range;
determining, for each detector of the plurality of detectors from the corresponding detector scan data, a second detector count rate occurring in a second window spanning a second energy range, the second energy range being different from the first energy range;
calculating, for each detector of the plurality of detectors, a detector count loss correction factor, based on the determined detector first count rate for the detector and the determined second detector count rate for the detector;
calculating a particular count loss correction factor based on the calculated plurality of detector count loss correction factors corresponding to the plurality of detectors; and
reconstructing an image based on the acquired scan data and the calculated particular count loss correction factor.

(9) The method of (8), wherein the step of determining the first detector count rate for each detector comprises determining, as the first detector count rate, a total count rate of the detector in the first energy window, which is a photoelectric window.

(10) The method of (8), wherein the step of determining the second detector count rate for each detector comprises determining, as the second detector count rate, a total count rate of the detector in the second energy window, which spans an entirety of the energy spectrum for the radiation diagnosis apparatus.

(11) The method of (8), wherein the calculating step further comprises calculating, for each detector of the plurality of detectors, an effective singles detector count rate as a weighted combination of the first detector count rate and the second detector count rate.

(12) A radiation diagnosis apparatus, comprising:
circuitry configured to
  acquire scan data from a scan of a patient performed using a scanning apparatus of the radiation diagnosis apparatus;
  determine, from the acquired scan data, a first count rate occurring in a first energy window spanning a first energy range;
  determine, from the acquired scan data, a second count rate occurring in a second window spanning a second energy range, the second energy range being different from the first energy range;
  calculate a particular count loss correction factor based on the determined first count rate and the determined second count rate; and
  reconstruct an image based on the acquired scan data and the calculated particular count loss correction factor.

(13) The radiation diagnosis apparatus of (12), further comprising the scanning apparatus, which is configured to perform the scan of the patient to acquire scan data.

(14) The radiation diagnosis apparatus of (12), wherein the circuitry is further configured to, in determining the first count rate, determine, as the first count rate, a total count rate from all detectors in the radiation diagnosis apparatus in the first energy window, which is a photoelectric window.

(15) The radiation diagnosis apparatus of (12), wherein the circuitry is further configured to, in determining the second count rate, determine, as the second count rate, a total count rate from all detectors in the radiation diagnosis apparatus in the second energy window, which spans an entirety of the energy spectrum for the radiation diagnosis apparatus.

(16) The radiation diagnosis apparatus of (12), wherein the circuitry is further configured to, in calculating the particular count loss correction factor, calculate an effective singles count rate as a weighted combination of the first count rate and the second count rate.

(17) The radiation diagnosis apparatus of (16), wherein the circuitry is further configured to, in calculating the effective singles count rate, calculate the effective singles count rate using weights that are predetermined so as to minimize a count loss correction error calculated for a plurality of phantoms.

(18) The radiation diagnosis apparatus of (16), wherein the circuitry is further configured to, in calculating the particular count loss correction factor, determine a singles count loss correction factor based on the calculated effective singles count rate by applying the calculated effective singles count rate to a predetermined count loss correction function.

(19) The radiation diagnosis apparatus of (18), wherein the circuitry is further configured to determine, as the particular count loss correction factor, a pairs count loss correction factor, based on the determined singles count loss correction factor.

(20) The method of (1), wherein the calculating step further comprises calculating the particular count loss correction factor by directly applying the determined first count rate and the determined second count rate to a multidimensional function or lookup table.

(21) A method for count loss correction based on detector dead time in a radiation diagnosis apparatus, the method comprising:
acquiring scan data from a scan of a patient performed using the radiation diagnosis apparatus;
determining, from the acquired scan data, a first measured quantity related to a first energy range;
determining, from the acquired scan data, a second measured quantity related to a second energy range, the second energy range being different from the first energy range, or the second measured quantity relating to the first energy range, but differently from the first measured quantity;
calculating a particular count loss correction factor based on the determined first measured quantity and the determined second measured quantity; and
reconstructing an image based on the acquired scan data and the calculated particular count loss correction factor.

Numerous modifications and variations of the present disclosure are possible in light of the above teachings. It is therefore to be understood that within the scope of the appended claims, the inventions can be practiced otherwise than as specifically described herein.

The invention claimed is:

1. A method for count loss correction based on detector dead time in a radiation diagnosis apparatus, the method comprising:
   acquiring scan data from a scan of a patient performed using the radiation diagnosis apparatus;
   determining, from the acquired scan data, a first count rate occurring in a first energy window spanning a first energy range;
   determining, from the acquired scan data, a second count rate occurring in a second window spanning a second energy range, the second energy range being different from the first energy range;
   calculating a particular count loss correction factor based on the determined first count rate and the determined second count rate; and
   reconstructing an image based on the acquired scan data and the calculated particular count loss correction factor,
   wherein the calculating step further comprises calculating an effective singles count rate as a weighted combination of the first count rate and the second count rate.

2. The method of claim 1, wherein the step of determining the first count rate comprises determining, as the first count rate, a total count rate from all detectors in the radiation diagnosis apparatus in the first energy window, which is a photoelectric window.

3. The method of claim 1, wherein the step of calculating the effective singles count rate comprises calculating the effective singles count rate using weights that are predetermined so as to minimize a count loss correction error calculated for a plurality of phantoms.

4. The method of claim 1, wherein the calculating step further comprises determining a singles count loss correction factor based on the calculated effective singles count rate by applying the calculated effective singles count rate to a predetermined count loss correction function.

5. The method of claim 4, wherein the calculating step further comprises determining, as the particular count loss correction factor, a pairs count loss correction factor, based on the determined singles count loss correction factor.

6. The method of claim 1, wherein the calculating step further comprises calculating the particular count loss correction factor by directly applying the determined first count rate and the determined second count rate to a multidimensional function or lookup table.

7. A method for count loss correction based on detector dead time in a radiation diagnosis apparatus, the method comprising:
   acquiring scan data from a scan of a patient performed using the radiation diagnosis apparatus;
   determining, from the acquired scan data, a first count rate occurring in a first energy window spanning a first energy range;
   determining, from the acquired scan data, a second count rate occurring in a second window spanning a second energy range, the second energy range being different from the first energy range;
   calculating a particular count loss correction factor based on the determined first count rate and the determined second count rate; and
   reconstructing an image based on the acquired scan data and the calculated particular count loss correction factor,
   wherein the step of determining the second count rate comprises determining, as the second count rate, a total count rate from all detectors in the radiation diagnosis apparatus in the second energy window, which spans an entirety of the energy spectrum for the radiation diagnosis apparatus.

8. A method for count loss correction based on detector dead time in a radiation diagnosis apparatus, the method comprising:
   acquiring, for each detector of a plurality of detectors in the radiation diagnosis apparatus, corresponding detector scan data for the detector, from a scan of a patient performed using the radiation diagnosis apparatus;
   determining, for each detector of the plurality of detectors from the corresponding detector scan data, a first detector count rate occurring in a first energy window spanning a first energy range;
   determining, for each detector of the plurality of detectors from the corresponding detector scan data, a second detector count rate occurring in a second window spanning a second energy range, the second energy range being different from the first energy range;
   calculating, for each detector of the plurality of detectors, a detector count loss correction factor, based on the determined first detector first count rate for the detector and the determined second detector count rate for the detector;
   calculating a particular count loss correction factor based on the calculated plurality of detector count loss correction factors corresponding to the plurality of detectors; and
   reconstructing an image based on the acquired scan data and the calculated particular count loss correction factor,
   wherein the calculating step further comprises calculating, for each detector of the plurality of detectors, an effective singles detector count rate as a weighted combination of the first detector count rate and the second detector count rate.

9. The method of claim 8, wherein the step of determining the first detector count rate for each detector comprises determining, as the first detector count rate, a total count rate of the detector in the first energy window, which is a photoelectric window.

10. The method of claim 8, wherein the step of determining the second detector count rate for each detector comprises determining, as the second detector count rate, a total count rate of the detector in the second energy window, which spans an entirety of the energy spectrum for the radiation diagnosis apparatus.

11. A radiation diagnosis apparatus, comprising:
    circuitry configured to
       acquire scan data from a scan of a patient performed using a scanning apparatus of the radiation diagnosis apparatus;
       determine, from the acquired scan data, a first count rate occurring in a first energy window spanning a first energy range;
       determine, from the acquired scan data, a second count rate occurring in a second window spanning a second energy range, the second energy range being different from the first energy range;
       calculate a particular count loss correction factor based on the determined first count rate and the determined second count rate; and reconstruct an image based on the acquired scan data and the calculated particular count loss correction factor, wherein the circuitry is further configured to, in calculating the particular count loss correction factor, calculate an effective singles count rate as a weighted combination of the first count rate and the second count rate.

12. The radiation diagnosis apparatus of claim 11, further comprising the scanning apparatus, which is configured to perform the scan of the patient to acquire scan data.

13. The radiation diagnosis apparatus of claim 11, wherein the circuitry is further configured to, in determining the first count rate, determine, as the first count rate, a total count rate from all detectors in the radiation diagnosis apparatus in the first energy window, which is a photoelectric window.

14. A radiation diagnosis apparatus comprising:
circuitry configured to
acquire scan data from a scan of a patient performed using a scanning apparatus of the radiation diagnosis apparatus;
determine, from the acquired scan data, a first count rate occurring in a first energy window spanning a first energy range;
determine, from the acquired scan data, a second count rate occurring in a second window spanning a second energy range, the second energy range being different from the first energy range;
calculate a particular count loss correction factor based on the determined first count rate and the determined second count rate; and
reconstruct an image based on the acquired scan data and the calculated particular count loss correction factor, wherein the circuitry is further configured to, in determining the second count rate, determine, as the second count rate, a total count rate from all detectors in the radiation diagnosis apparatus in the second energy window, which spans an entirety of the energy spectrum for the radiation diagnosis apparatus.

15. The radiation diagnosis apparatus of claim 14, wherein the circuitry is further configured to, in calculating the effective singles count rate, calculate the effective singles count rate using weights that are predetermined so as to minimize a count loss correction error calculated for a plurality of phantoms.

16. The radiation diagnosis apparatus of claim 14, wherein the circuitry is further configured to, in calculating the particular count loss correction factor, determine a singles count loss correction factor based on the calculated effective singles count rate by applying the calculated effective singles count rate to a predetermined count loss correction function.

17. The radiation diagnosis apparatus of claim 16, wherein the circuitry is further configured to determine, as the particular count loss correction factor, a pairs count loss correction factor, based on the determined singles count loss correction factor.

* * * * *